United States Patent [19]
Weaver

[11] Patent Number: 5,458,112
[45] Date of Patent: Oct. 17, 1995

[54] BILIARY BIOPSY DEVICE

[75] Inventor: George W. Weaver, East Earl, Pa.

[73] Assignee: Arrow Precision Products, Inc., Reading, Pa.

[21] Appl. No.: 290,147

[22] Filed: Aug. 15, 1994

[51] Int. Cl.⁶ .................................................. A61B 10/00
[52] U.S. Cl. ........................ 128/753; 128/754; 606/171
[58] Field of Search ................................. 128/751, 752, 128/753, 754; 606/170, 167, 171

[56] References Cited

U.S. PATENT DOCUMENTS

| | | | |
|---|---|---|---|
| 4,340,066 | 7/1982 | Shah | 128/749 |
| 4,651,753 | 3/1987 | Lifton . | |
| 4,907,598 | 3/1990 | Bauer | 128/753 |
| 5,090,419 | 2/1992 | Palestrant | 128/754 |
| 5,106,364 | 4/1992 | Hayafuji et al. | 604/22 |
| 5,127,419 | 7/1992 | Kaldany | 128/754 |
| 5,190,542 | 3/1993 | Nakao et al. . | |
| 5,327,896 | 7/1994 | Schmieding | 128/753 |

FOREIGN PATENT DOCUMENTS 0513446  11/1992  United Kingdom .................... 128/754

OTHER PUBLICATIONS

"Endoscopic Needle Aspiration Biopsy at ERCP In The Diagnosis Of Strictures", Gastrointesinal Endoscopy, vol. 38, No. 5, 1992.

Primary Examiner—Angela D. Sykes
Assistant Examiner—Eric F. Winakur
Attorney, Agent, or Firm—Amster, Rothstein & Ebenstein

[57]  ABSTRACT

A surgical instrument assembly for use in a biopsy operation includes a flexible tube having a pair of opposed ends and a substantially rigid, cylindrical cutter having a distal end, a proximal end secured to one of the opposed tube ends for longitudinal movement therewith, and a sidewall connecting the distal and proximal ends. The cutter sidewall defines at least one recess having a barb at the outer distal end thereof for separating biopsy tissue from a patient and maintaining the separated tissue in the recess during movement of the cutter. The other of the opposed tube ends is optionally operatively securable to a vacuum source for applying a vacuum to the recess via a longitudinal cavity in the tube and cutter member. An unloading stylet may be disposed within the longitudinal cavity in the cutter for sliding movement relative thereto between a proximal position relative to the recess and a distal position within the recess, whereby movement of the unloading stylet from the proximal position to the distal position ejects from the recess any separated tissue therein.

12 Claims, 5 Drawing Sheets

BILIARY BIOPSY DEVICE

BACKGROUND OF THE INVENTION

The present invention relates to a surgical instrument assembly for use in a biopsy operation, and more particularly to a biliary biopsy device for severing and retrieving portions of lesions or other clumps of organic tissue from a patient's internal organs.

Differentiating malignant biliary strictures from benign ductal lesions can be a diagnostic challenge. For example, malignant-appearing bile duct strictures are commonly encountered during endoscopic retrograde cholangeopancreatography ("ERCP") in patients presenting with signs and symptoms of biliary obstruction or pancreatitis. However, benign etiologies are often indistinguishable radiologically from malignancy, emphasizing the importance of histologic diagnosis (i.e. taking a biopsy).

Present methods of taking a biopsy in the biliary tree frequently rely on the use of cytology brushes, needle aspiration, and in some instances forceps for severing and recovering a portion of a lesion or other growth of interest. Unfortunately, each of these procedures is characterized by its own deficiencies, limitations and difficulties such that none of them is considered a fully acceptable biopsy device. In particular, these alternative devices tend to be difficult to use and/or remove such a small portion of the lesion or other growth that the characterization of the removed organic tissue is unreliable or difficult.

Accordingly, it is an object of the present invention to provide a biopsy device suitable for use in the biliary tree and like small ducts.

Another object is to provide such a device which yields a specimen of a desirably large volume for performing a biopsy analysis.

A further object is to provide such a device which is especially well suited for use in a blind biopsy operation.

It is another object of the present invention to provide such a device which, in a preferred embodiment, safely captures the biopsied specimen yet facilitates ejection of the specimen from the device when desired.

It is a further object to provide such device which is simple and economical to manufacture and use.

SUMMARY OF THE INVENTION

It has now been found that the above and related objects of the present invention are attained in a surgical instrument assembly for use in a biopsy operation comprising in a first embodiment a flexible member and a cutting member. The flexible member has a pair of opposed ends. The cutting member has a distal end, a proximal end secured to one of the opposed flexible member ends for longitudinal movement therewith, and a sidewall connecting the distal and proximal ends. The cutting member sidewall defines a recess having at least one barb for separating biopsy tissue from a patient and maintaining the separated tissue in the recess during movement of the cutting member.

In a preferred first embodiment, there are a plurality of recesses spaced apart about the circumference of the cutting member and spaced apart along the longitudinal axis of the cutting member, the plurality preferably being three. Each recess preferably also has a proximally-facing barb at the outer distal end thereof and, optionally, a distally-facing barb at the outer proximal end thereof. The distal end of the cutting member optionally defines a distal recess at the tip thereof for separating biopsy tissue from the patient as the cutting member is moved distally and maintaining the separated tissue in the distal recess as the cutting member is moved proximally.

In another preferred first embodiment, the assembly additionally includes a movable actuator secured to the other of the opposed flexible member ends for longitudinally moving the same therewith. A longitudinal cavity is formed in the flexible member and the cutting member, and an unloading styler is disposed within the cutting member longitudinal cavity for sliding movement relative thereto between proximal and distal positions relative to the recesses. Thus movement of the styler from the proximal position to the distal position ejects from the recess any separated tissue located in the cutting member longitudinal cavity. The actuator, upon actuation, causes sliding movement of the styler between the proximal position and the distal position. The cutting member longitudinal cavity and the flexible member longitudinal cavity are in operative communication, and means linking the actuator and the stylet for longitudinal movement as a unit extends through both the longitudinal cavities.

Alternatively, the assembly additionally includes means operatively secured to the other of the opposed flexible member ends for applying a vacuum to the recess via the longitudinal cavities of the flexible and cutting members.

The present invention also encompasses a second embodiment of the present invention wherein the surgical instrument assembly for use in a biopsy operation comprises a flexible, hollow tubular member having a pair of opposed ends and a sidewall therebetween defining a longitudinal cavity communicating with the opposed ends. A flexible, elongate member defines a pair of opposed ends, the elongate member extending through the tubular member. A substantially rigid, cylindrical outer member defines a distal end, a proximal end secured to one of the opposed tubular member ends for longitudinal movement therewith, and a sidewall connecting the distal and proximal ends. The outer member sidewall and the outer member proximal end define an outer member longitudinal cavity communicating with the tubular member longitudinal cavity. The outer member sidewall also defines a side recess. A substantially rigid, cylindrical inner member is configured and dimensioned for sliding movement within and relative to the outer member. The inner member defines a distal end, a proximal end secured to one of the opposed ends of the elongate member for movement therewith, and a sidewall connecting the distal and proximal ends. The inner member sidewall defines a recess having a barb for separating the biopsy tissue from the patient during movement of the inner member from a first position and maintaining the separated tissue in the inner member recess. The inner member recess communicating with the outer member side recess in the first position. An actuator is secured to the other of the opposed ends of the tubular and elongate members for longitudinal movement therewith, the actuator additionally including means for moving the elongate member and the inner element relative to the tubular member and the outer element.

The present invention further encompasses a third embodiment of the present invention wherein the surgical instrument assembly for use in a biopsy operation comprises a flexible, hollow tubular member having a pair of opposed ends and a sidewall therebetween defining a longitudinal cavity communicating with the opposed ends. A flexible, elongate member defines a pair of opposed ends, the elongate member extending through the tubular member. A substantially rigid, cylindrical outer member defines a distal end, a proximal end secured to one of the opposed tubular member ends for longitudinal movement therewith, and a sidewall connecting the distal and proximal ends. The outer member sidewall and the outer member proximal end defines an outer member longitudinal cavity communicating with the tubular member longitudinal cavity. The outer member sidewall also defines a distal recess at the distal end of the outer member. A substantially rigid, cylindrical inner member is configured and dimensioned for sliding movement within and relative to the outer member. The inner member defines a distal end, a proximal end secured to one of the opposed ends of the elongate member for movement therewith, and a sidewall connecting the distal and proximal ends. The inner member sidewall defines a recess having a barb for separating the biopsy tissue from the patient and maintaining the separated tissue in the inner member recess during movement of the inner member through said outer member distal recess from a position outside of said outer member to a position within said outer member. An actuator is secured to the other of the opposed ends of the tubular and elongate members for longitudinal movement therewith, the actuator additionally including means for moving the elongate member and the inner element relative to the tubular member and the outer element.

In both the second and third embodiments the recess of the inner member sidewall preferably defines a proximally-facing barb means at the outer distal end thereof.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Referring now to the drawing, and in particular the FIGS. 1–5 thereof, therein illustrated is a surgical instrument assembly according to the present invention, generally designated by the reference numeral 10. The assembly 10 may be used for biopsies within any internal organs, but is especially suited for biopsies taken within the biliary tree where the ducts are very small.

The assembly 10 comprises a flexible, preferably hollow tubular member, generally designated 12, and a substantially rigid, cylindrical cutting member, generally designated 14. The flexible/tubular member 12 defines a pair of opposed ends—namely, a distal end 16 and a proximal end 18—and a sidewall 20 defining a longitudinal cavity 22 communicating with the opposed tubular member ends 16, 18. The tubular member 12 is preferably characterized by a high level of flexibility to enable it to be passed through an endoscope and into the veins or other interior portions of the human body. It is preferably transparent and non-reactive with bodily fluids. Generally the tubular member 12 is 200–220 cm in length. Where the tubular member is to be passed into the biliary tree, it preferably has a maximum outside diameter of 0.035 inches so as to enable insertion into the biliary tree. The tubular member 12 is made of plastic or metal tubing affording the requisite flexibility. As tubular members of this type are well known in the surgical art, it not deemed necessary to set forth herein further details thereof.

The cutting member 14 is substantially rigid and about 1–2 cm in length. It has a distal end 30, a proximal end 32 secured to the tubular member distal end 16 for longitudinal movement therewith, and a sidewall 34 defining a longitudinal cavity 35 connecting the cutting member ends 32, 30. The cutting member sidewall 34 defines at least one longitudinally-extending side recess 40 (and as illustrated three such side recesses) having a proximally facing barb means 42 at the outer distal end of the side recess 40. The barb means 42 is used for separating biopsy tissue (such as a portion of a lesion or other clump of organic tissue 44) from a cavity or biliary duct 46 of a patient during movement of the cutting member 14 in the proximal direction and maintaining the separated tissue in the side recess Preferably there are a plurality of the recesses 40 equiangularly spaced apart so that the three illustrated recesses 40 are spaced apart on the circumference of the cutting member by 120°. The recesses are preferably equidistally spaced apart along the longitudinal axis of the cutting member 14. The preferred spacing of the recesses increases the chances of obtaining a biopsy especially in blind procedures. While reciprocating movement of a cutting member 14 having only a proximally-facing barb means 42 is sufficient to effect severance of a lesion 44 or like growth from the duct wall 46, preferably the recess 40 additionally includes a distally-facing barb means 48 at the outer proximal end of recess 40. When the side recess 40 is provided with oppositely facing barb means 42, 48, it acts as a broach to separate protruding lesion tissue 44 from the duct wall 46 as the cutting member 14 is reciprocated within the duct 46. The presence of oppositely facing barb means 42, 48 within a side recess 40 enables the recess to contribute to the severance of the lesion 44 from the duct wall 46 in both stroke directions, thus increasing the rate of severance and thereby minimizing the overall operating time.

In a preferred embodiment of the present invention, the distal end 30 of the cutting member 14 defines a distal recess 50 at the tip thereof for separating biopsy tissue from the duct of a patient as the cutting member 14 is moved distally and maintaining the separated tissue in the distal recess 50 as the cutting member is moved proximally. While typically the distal edge of the cutting member sidewall 34 is sufficient to act as a ring punch and sever the biopsy tissue from the patient during distal movement of the cutting member 14, if desired the distal end of the sidewall 34 may be beveled inwardly to form a sharp edge to assist in retention of any separated tissue within the distal recess 50.

The size of each individual side recess 40 and distal recess 50 is selected to enable biopsy specimens of adequate size to be obtained. The biopsy material 44 removed by a side recess 40 is stored within that recess and to some degree within the longitudinal cavity 35 defined by the cutting member sidewall 34, while the lesion material removed by the distal recess 50 is stored therein and possibly within the same cavity 35.

As will be appreciated by those skilled in the surgical art, the provision of a plurality of side recesses 40 facilitates obtaining a specimen of a lesion extending from a duct wall when the surgeon is operating blindly, as he must in the biliary tree. The widely angularly spaced apart side recesses 40 obtain specimens from angularly spaced segments of the duct wall simultaneously. Additionally, when a distal recess 50 is provided, the distal recess secures specimens of blockages or lesions which have grown across the travel path of the cutting member 14. Accordingly, the assembly of the first embodiment is particularly well adapted for use in blind operations.

Figures 1, 2:
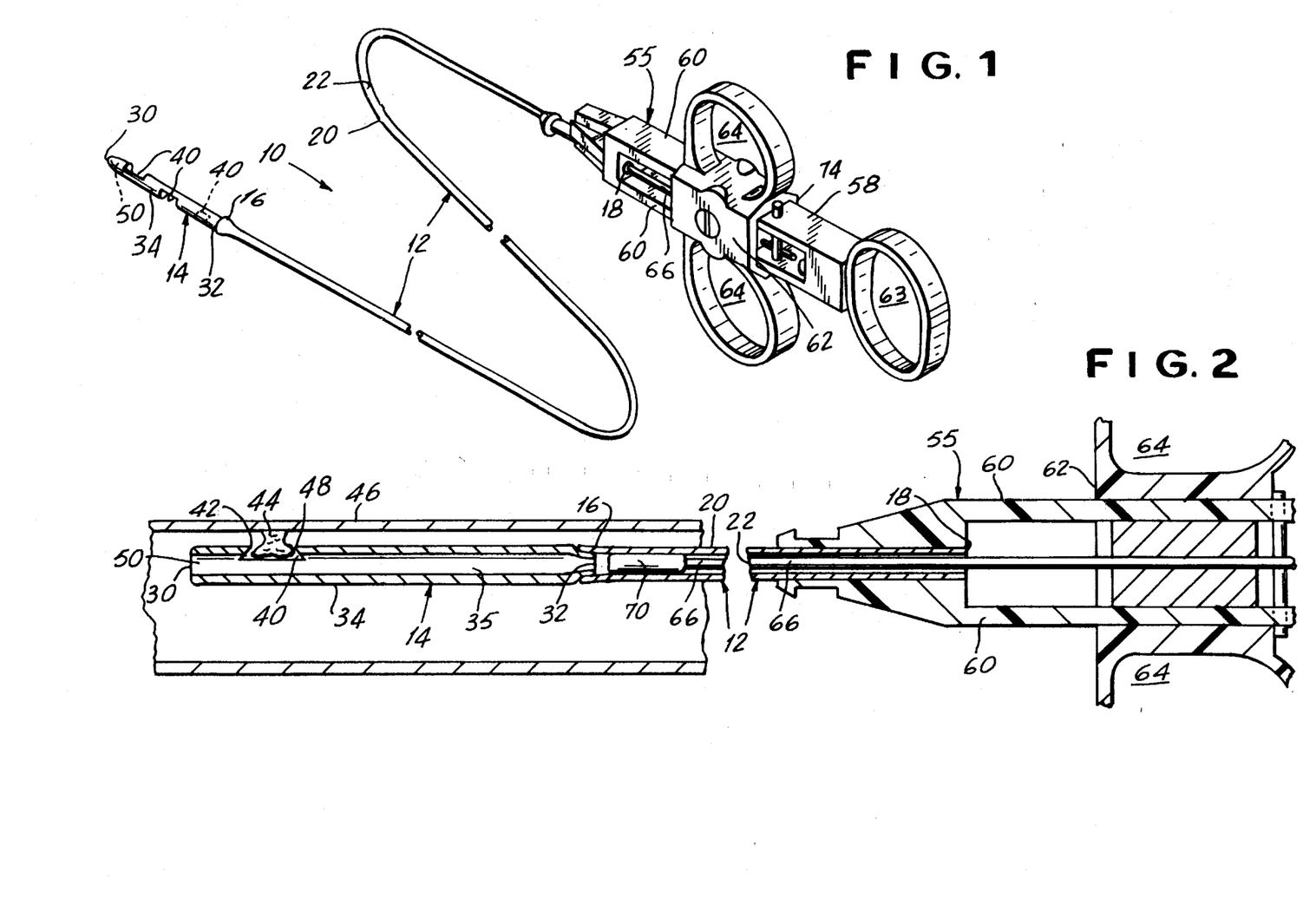
FIG. 1 is a fragmentary isometric view of a first embodiment of a biopsy device according to the present invention.
FIG. 2 is a fragmentary sectional view thereof showing the cutting member disposed in a biliary duct and capturing a portion of a lesion, with the unloading stylet in a retracted position.

In order to facilitate reciprocating movement of the assembly 10 (consisting of the tubular member 12 and cutting member 14), a movable actuator, generally designated 55, is preferably secured to the proximal end 18 of the tubular member 12 for longitudinally moving the same therewith. Once the assembly 10 has been passed through the appropriate lumen of the endoscope and further so that the cutting member 14 is at the desired location, the surgeon has only to grasp the actuator 55 and reciprocate the same in order to reciprocate the recesses 40, 50 of cutting member 14 (assuming that the tubular member 12 is of a suitable length so that there is no lost motion).

In a first preferred embodiment of the present invention, the actuator 55 comprises a body member or frame 58 which includes a pair of parallel rails 60 to which a slider member 62 is reciprocatably secured. Frame 58 has a thumb hole 63 at a proximal end, whereas slider member 62 has a pair of finger holes 64 and is fastened to the proximal end of a wire 66 which passes through the tubular member longitudinal cavity 22 and is in turn connected to an unloading styler 70 (best seen in FIGS. 2 and 3) disposed at the distal end 16 of the tubular member longitudinal cavity 12. Wire 66 is sufficiently flexible to bend with tubular member 12 during the negotiation thereby of curves or bends in a duct or organ during surgery.

Figures 3, 5:
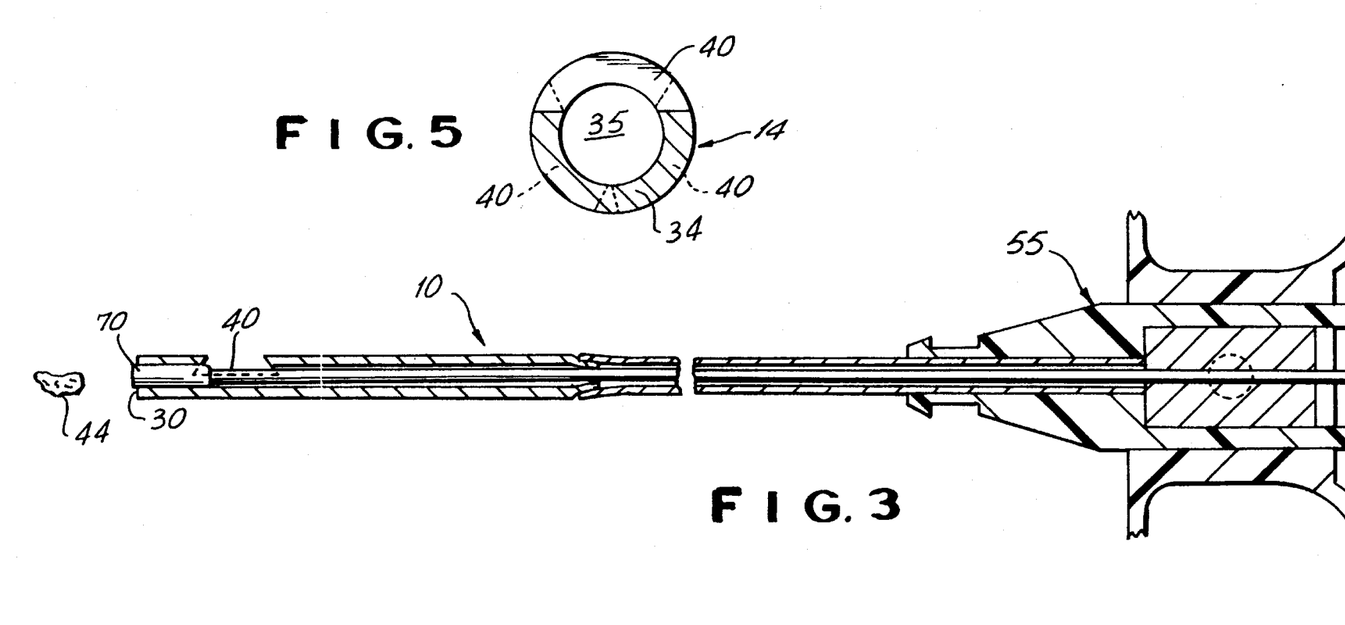
FIG. 3 is a sectional view similar to FIG. 2, but with the cutting member withdrawn from the biliary duct and the unloading stylet in a distal position ejecting a biopsy specimen.
FIG. 5 is a sectional view thereof taken along the line 5—5 of FIG. 4.
Figure 4:
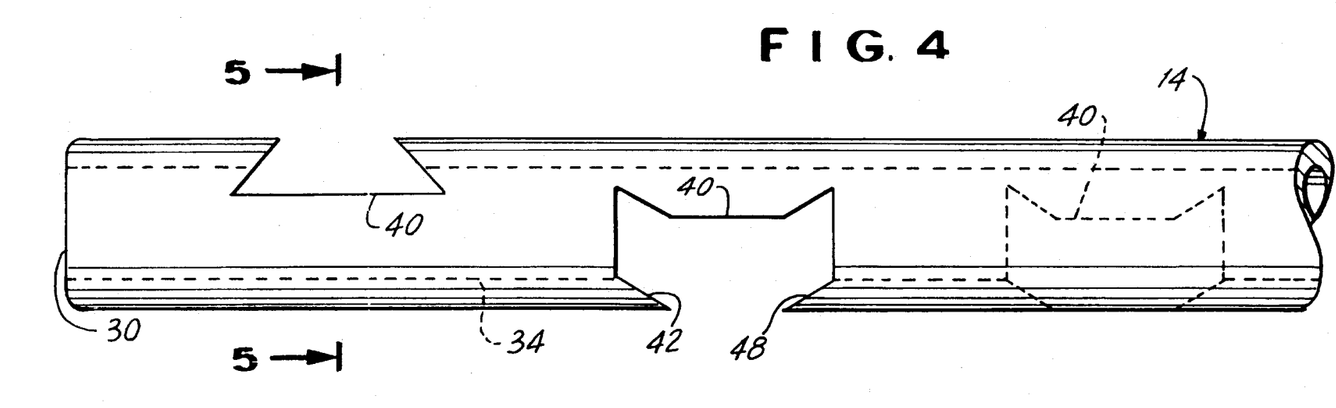
FIG. 4 is a fragmentary side elevational view of the distal end of the biopsy device.

The unloading procedure is illustrated in FIG. 3 where the slider member 62 has been moved distally on the frame 58 so that the stylet 70 has moved distally to eject the biopsy tissue 44 from the cutting member 14. The unloading styler 70 is configured and dimensioned for passage from the adjacent tubular member longitudinal cavity 22 into the cutting member 14 longitudinal cavity 35 from the proximal end 32 thereof all the way to the distal end 30. The unloading stylet 70 is disposed for sliding movement relative to the cutting member 14 between a proximal position, proximal to the most proximal side recess 40, and a distal position, distal to the most distal side recess 40 (and preferably about 0.5 mm distal to the tubular member end 30), so that movement of the styler 70 from the proximal position to the distal position ejects distally from each of the side recesses 40 any separated tissue therein via longitudinal cavity 35. The same movement of the stylet 70 also ejects distally from the distal recess 50 any separated tissue therein. This unloading movement of the stylet 70 can be effected by the surgeon once he has withdrawn the assembly 10 from the patient and appropriately positioned the cutting member 14 for receipt and collection of the ejected separated tissue. The cutting member longitudinal cavity 35 and the tubular member longitudinal cavity 22 are in operative communication, with the wire 66 acting as the means to link the actuator 55 and the styler 70 for longitudinal movement as a unit, the wire extending through the entire longitudinal cavity 22 and at least partially through the longitudinal cavity 35.

The actuator 55 preferably includes a stop 74 which limits withdrawal of the slider member 62 relative to the frame 58 so that the length of the travel path of the slider member 62 is equal to the desired length of the travel path of the unloading stylet 70. Thus the stop ensures that the unloading stylet 70 never totally emerges from the cutting member distal end 30.

Figure 10:
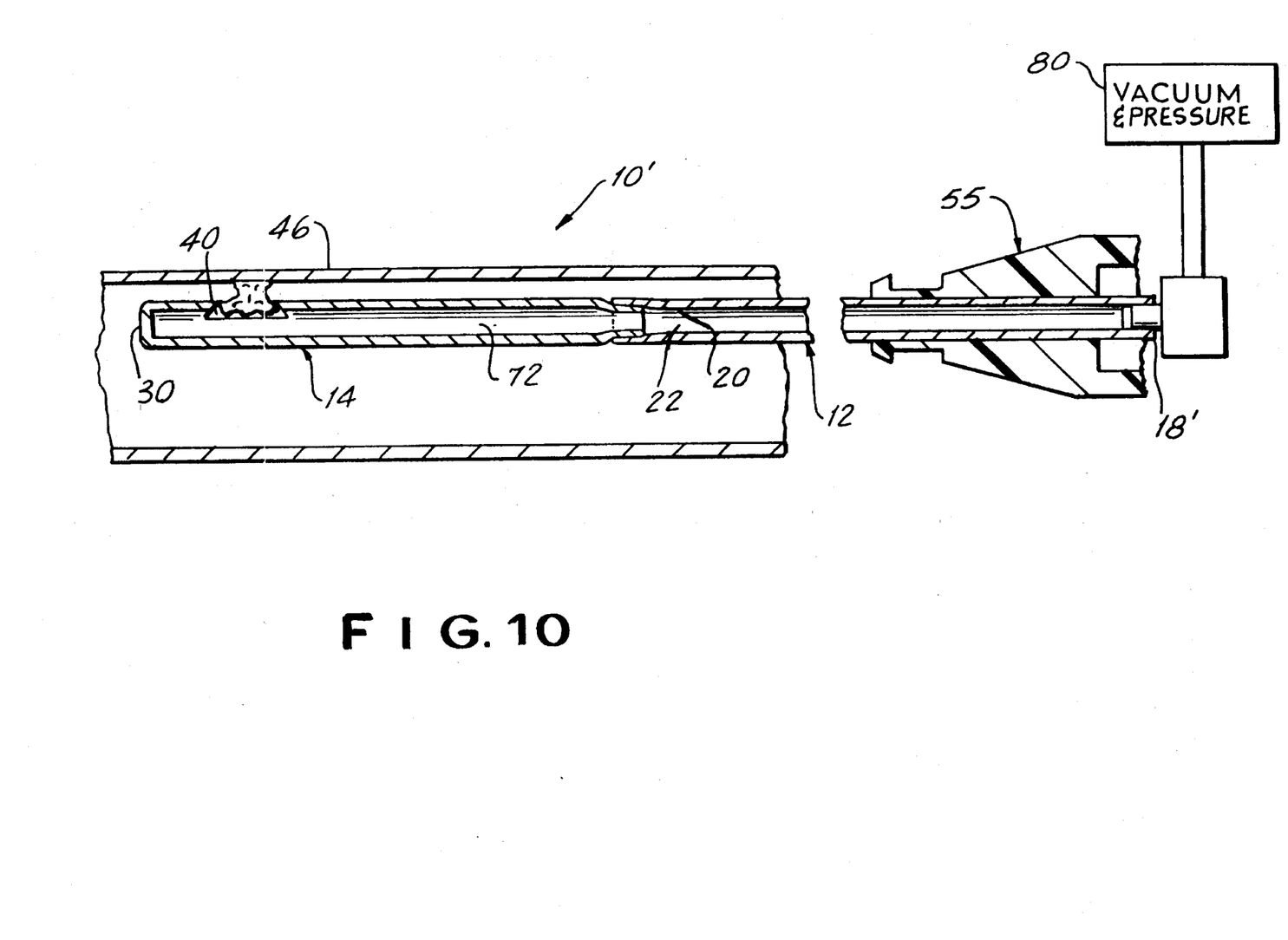
FIG. 10 is a fragmentary sectional view of a variant of the first embodiment.

Referring now to FIG. 10, therein illustrated is a variant of the first embodiment 10, generally designated 10'. In the variant 10' there is no unloading stylet 70 or associated wire 66. Instead, the distal end 18' of the tubular member 12 is in operative communication with an external vacuum source 80 which applies a vacuum through both the tubular member longitudinal cavity 22 and the cutting member longitudinal cavity 35. The resultant negative pressure within the side recesses 40 (only one being shown) and the distal recess 50 (none shown) assists in drawing the head of the lesion or other growth into the aforementioned recesses. The drawing effect is, of course, enhanced as the applied vacuum or negative pressure is increased and as the number of recesses 40, 50 in the cutting member 14 is reduced. Typically a reduction in the air pressure of 26–28 inches Hg is sufficient to assist entry of the lesions into the recesses. The severed tissue may be removed from the side recess or recesses 40 or any distal recess 50 manually. Alternatively, where the first vacuum source 80 is easily convertible to a positive pressure source, the positive pressure source may be used to easily and rapidly eject the severed tissue from the recesses 40, 50.

Where the size of the unloading stylet 70 and associated wire 66 permits, the unloading stylet 70 and associated wire 66 may be hollow and the vacuum drawn therethrough. However, an opening in the unloading stylet 70 typically reduces its efficiency as a means of ejecting severed tissue from the cutting member 14. Where the vacuum source 80 is easily converted to a positive pressure source, however, the variant 10° can more than compensate for the opening in the unloading stylet 70 by switching from a vacuum source to a pressure source once the assembly 10 has been removed from the patient. The positive pressure introduced through the tubular member longitudinal cavity 22 and into the cutting member longitudinal cavity 35 will assist in dislodgment of any severed tissue present in the recesses 40, 50 after the cutting member 14 has been introduced into a container for catching the discharged severed tissue.

Whereas the first embodiment 10, 10' relies upon the recesses 40, 50 to effectuate separation of the lesion or other growth 44 from the duct wall 46 (due to the use of barb means 42 or 42 and 48 defined by the recesses), the second and third embodiments described hereinbelow do not employ barbed recesses and instead use a separately reciprocatable inner cutter disposed within the outer member 14 (formerly referred to as the "cutting member 14") for severing and transporting the severed biopsy tissue.

Figure 6:
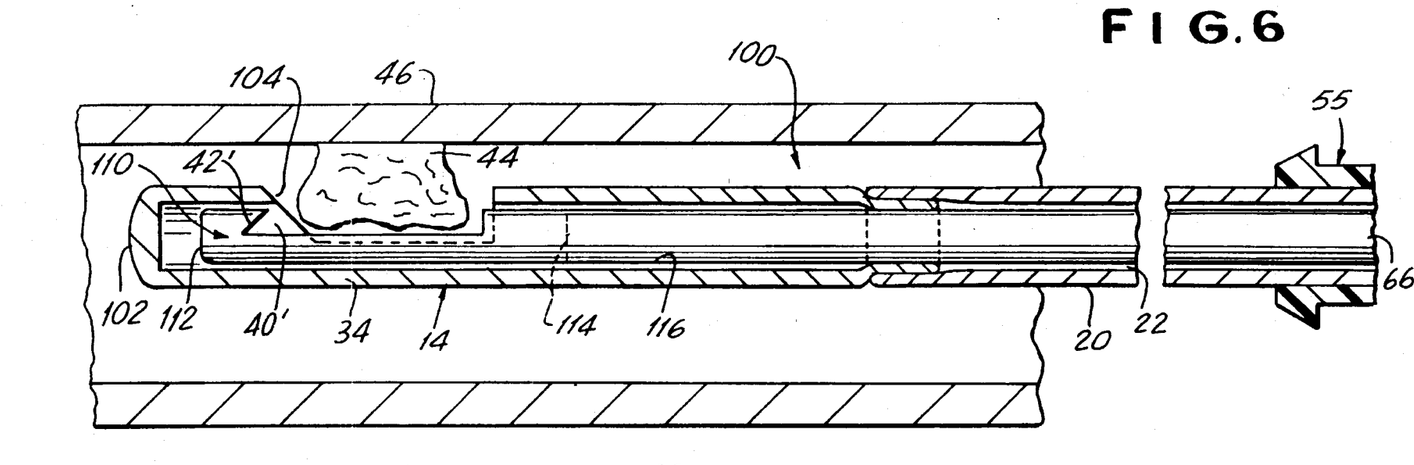
FIG. 6 is a fragmentary sectional view of a second embodiment of the present invention with the distal end of the biopsy device disposed in a biliary duct and with the cutter in a distal position.
Figure 7:
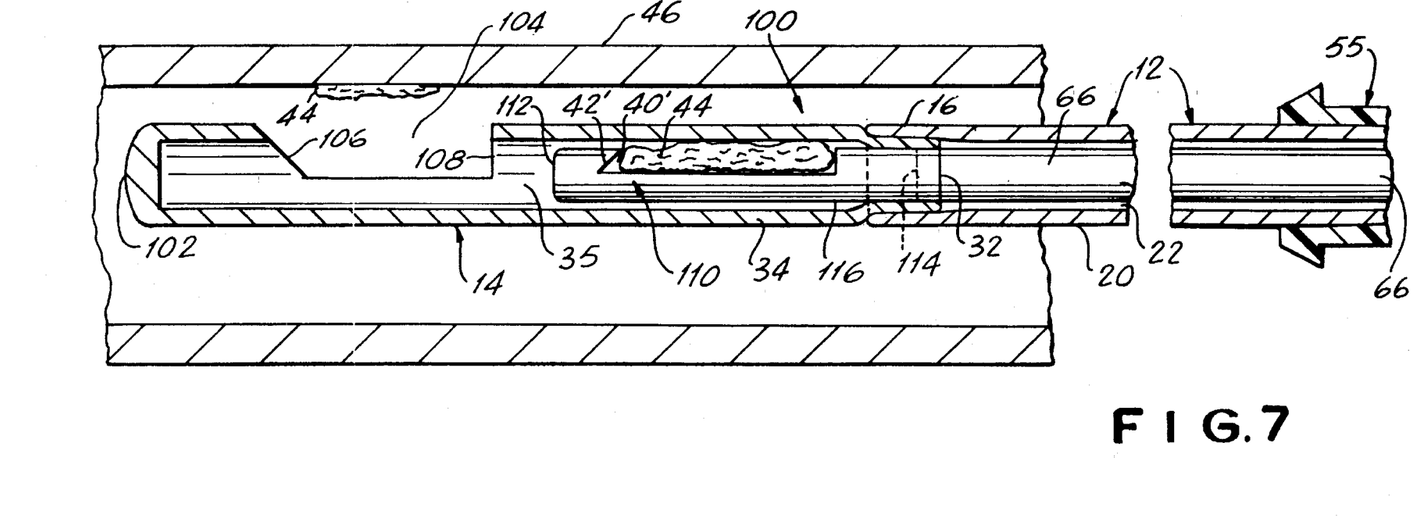
FIG. 7 is a view thereof similar to FIG. 6, but with the cutter in a retracted position.

Referring now to FIGS. 6 and 7, therein illustrated is a second embodiment, generally designated 100, of a surgical instrument assembly according to the present invention. In the illustrations of the second and third embodiments, elements of similar function and/or configuration to elements of the first embodiment 10 have been identified by the same numeral. In the second embodiment 100, the distal end of the outer member 14 is closed by an end wall 102 (so that there is no distal end recess 50) and the side recess or recesses 104 are not barbed. Rather the distal wall of each side recess 104 slopes radially inwardly and proximally while the proximal wall is perpendicular to the longitudinal axis of outer member 14, although different transverse angles may be used for particular applications. In the second embodiment 100 the outer member 14 is not necessarily rigid as actual cutting of the tissue 44 from the duct wall 46 is performed by a cutter 110. The cutter 110 is a substantially rigid, cylindrical inner member configured and dimensioned for sliding movement within and relative to the outer member 14. The inner member 110 defines a distal end 112, a proximal end 114, and a sidewall 116 connecting the ends 112, 114. A flexible tubular member 66, which may simply be a wire, extends through the entire length of the tubular member longitudinal cavity 22 and is secured to the proximal end of cutter 110 for movement therewith. The cutter sidewall 116 defines a longitudinally-extending side recess 40' having a barb 42' at the outer distal end thereof for separating the biopsy tissue from the patient during movement of the cutter 110 in the proximal direction and maintaining the separated tissue 44 in the cutter recess 40'. An actuator 55 provides means for moving the inner tubular member 66 and the cutter 110, as a unit, relative to the outer tubular member 12 and the outer element 14, as a unit between the distal position (see FIG. 6) and the proximal position (see FIG. 7).

If desired, the recess 40' of cutter 110 may also be provided with a distally-faced barb means (not shown) at the outer proximal end thereof to assist in separating the biopsy tissue from the patient during movement of the cutter 110 in the distal direction. When the actuator 55 is positioned with the sliding member 62 in the distal position relative to the frame 58 (as illustrated in FIG. 3), the cutter 110 is in the distal position illustrated in FIG. 6 so that side recess 40' is adapted to receive the head of the lesion 44 through the side recess 104 of the outer tubular member 14. When the sliding member 62 of actuator 55 is then moved proximally relative to the frame 58 (as illustrated in FIGS. 1 and 2), the sliding member 62 retracts the inner tubular member 66 and the cutter 110 to the proximal position illustrated in FIG. 7 so that barb 42' severs the lesion 44 from the duct wall 46 and carries it into the longitudinal cavity 35 of the outer tubular member 14. Once the severed tissue 44 is in this position, the entire assembly 10 may be withdrawn from the patient. At this point the movement of the actuator 55 is reversed so that a distal movement of the sliding member 62 relative to the frame 58 causes distal movement of the inner tubular member 66 and cutter 110 until there is once again alignment between the side recesses 104 of the outer tubular member 14 and the side recess 40' of the cutter 110 so that the severed biopsy tissue is available for removal from the assembly 10 (this tissue removal position being similar to the position illustrated in FIG. 6).

Figure 8:
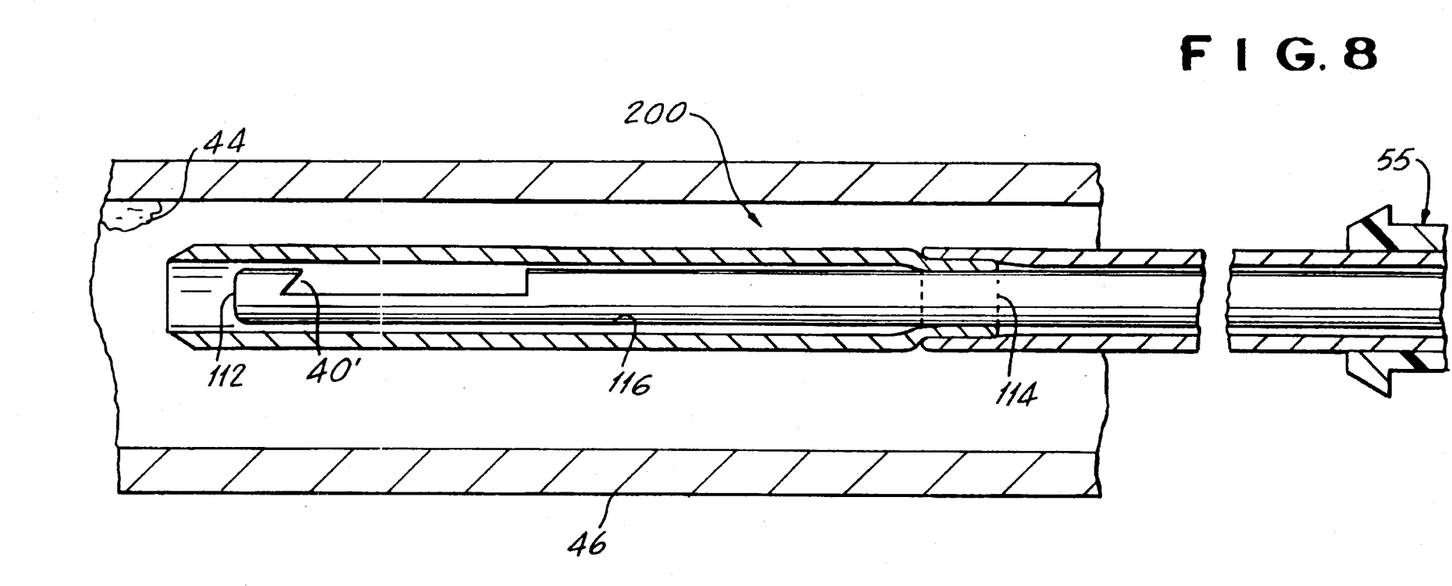
FIG. 8 is a view similar to FIG. 6 of a third embodiment of the present invention, with the cutter in a retracted position.
Figure 9:
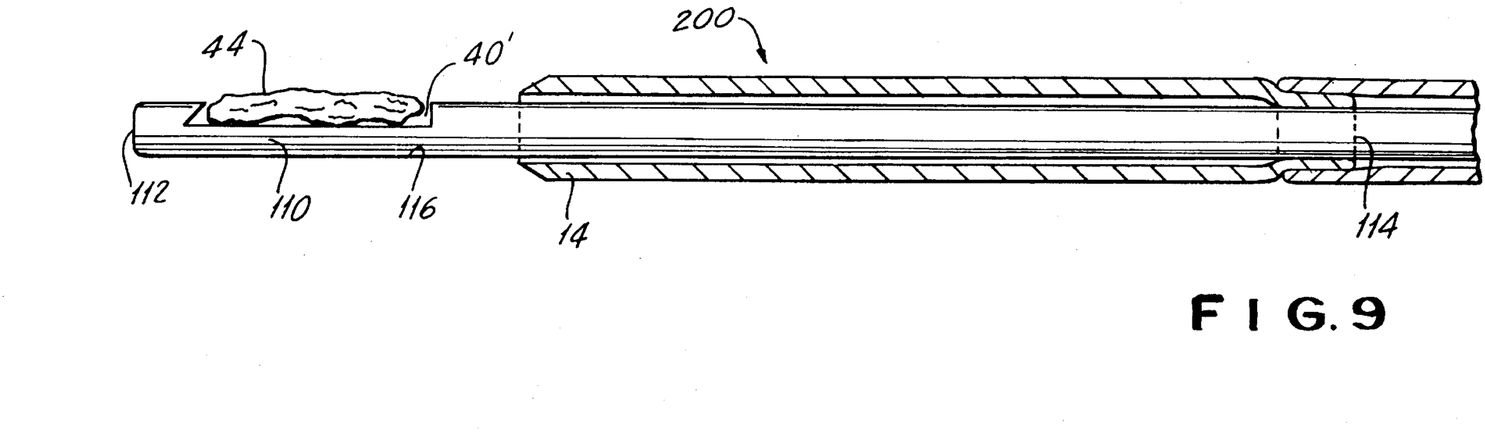
FIG. 9 is a view thereof similar to FIG. 8, but with the cutter in a distal position.

Referring now to FIGS. 8 and 9, therein illustrated is the third embodiment of the present invention, generally designated 200. The distal end of the outer tubular member 14 is open (that is, there is no blocking end wall 102), there is no side recess 104 in the outer tubular member, and the cutter 110 travels along a travel path which at one extreme (i.e., the proximal position) has the cutter 110 entirely disposed within the outer tubular member 14 (see FIG. 8) and at the other extreme (i.e., the distal position) has the recess 40' of the cutter 110 disposed entirely distally of the distal end of the outer tubular member 14. When the cutter 110 is in the distal position, lesions will enter the recess 40' and, as the cutter 110 is withdrawn to the proximal position, the distal barb will sever the lesions from the duct wall 46 so that the severed tissue 44 is withdrawn into the outer tubular member 14 with the cutter 110. If desired, the recess 40' of cutter 110 may also be provided with a distally-facing barb means (not shown) at the outer proximal end thereof to assist in separating the biopsy tissue from the patient during movement of the cutter 110 in the distal direction. Once the assembly 10 has been removed from the patient, the cutting member 110 is returned to its distal position (FIG. 9) for removal of the biopsy tissue 44 from the side recess 40' thereof.

To summarize, the present invention provides a biopsy device suitable for use in the biliary tree and like small ducts and is especially well suited for use in a blind biopsy operation. The present invention provides a specimen of a desirably large volume for performing a biopsy analysis and, in a preferred embodiment, safely captures the biopsy specimen yet facilitates ejection of the specimen from the device when desired. Further, the device is simple and economical to manufacture, maintain and use.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. A surgical instrument assembly for use in a biopsy operation, comprising:

(A) a flexible member having a pair of opposed ends and a longitudinal cavity communicating with said opposed ends;

(B) a substantially rigid, cylindrical cutting member having a distal end, a proximal end secured to one of said opposed flexible member ends for longitudinal movement therewith, and a sidewall connecting said distal and proximal ends, said cutting member sidewall defining a recess having barb means for separating biopsy tissue from a patient and maintaining the separated tissue in said recess during movement of said cutting member, said cutting member defining a longitudinal cavity communicating with said recess; and (C) an unloading stylet disposed within said cutting member longitudinal cavity for sliding movement relative thereto between a proximal position relative to said recess and a distal position beyond said recess;

whereby movement of said stylet from said proximal position to said distal position ejects from said recess any separated tissue therein.

2. The assembly of claim 1 wherein a said longitudinal cavity in said cutting member communicates with said recess and said flexible member longitudinal cavity, said assembly additionally including means operatively secured to the other of said opposed flexible member ends for applying a vacuum to said recess via said cutting member longitudinal cavity.

3. The assembly of claim 1 wherein there are a plurality of said recesses spaced apart about a circumference of said cutting member and spaced apart along a longitudinal axis of said cutting member.

4. The assembly of claim 3 wherein said plurality of said recesses is three.

5. The assembly of claim 1 wherein said distal end of said cutting member defines a distal recess and means for separating biopsy tissue from the patient as said cutting member is moved distally and maintaining the separated tissue in said distal recess when said cutting member is moved proximally.

6. The assembly of claim 1 wherein said recess has a distal end and a proximally-facing barb means at the distal end thereof.

7. The assembly of claim 1 additionally including a movable actuator secured to the other of said opposed flexible member ends for longitudinally moving the same therewith.

8. The assembly of claim 7 wherein said actuator includes means active upon actuation for causing sliding movement of said stylet between said proximal position and said distal position.

9. The assembly of claim 7 wherein said cutting member longitudinal cavity and said flexible member longitudinal cavity are in operative communication, and additionally includes means linking said actuator and said styler for longitudinal movement as a unit extending through both said longitudinal cavities.

10. A surgical instrument assembly for use in a biopsy operation, comprising:

(A) a flexible member having a pair of opposed ends and a longitudinal cavity communicating with said opposed ends;

(B) a substantially rigid, cylindrical cutting member having a distal end, a proximal end secured to one of said opposed flexible member ends for longitudinal movement therewith, and a sidewall connecting said distal and proximal ends, said cutting member sidewall defining a plurality of longitudinally-extending said recesses spaced apart about a circumference of said cutting member and spaced apart along a longitudinal axis of said cutting member, each side recess having a proximally-facing barb means at a distal end thereof and a distally-facing barb means at a proximal end thereof, for separating biopsy tissue from a patient during reciprocating movement of said cutting member and maintaining the separated tissue in each said side recess; a longitudinal cavity in said cutting member communicating with said side recesses, said cutting member longitudinal cavity and said flexible member longitudinal cavity being in operative communication;

(C) an actuator secured to the other of said opposed flexible member ends for longitudinally moving the same therewith;

(D) an unloading stylet disposed within said cutting member longitudinal cavity for sliding movement relative thereto between a proximal position relative to said recesses and a distal position relative to said recesses, whereby movement of said cutting member from said proximal position to said distal position ejects from each of said recesses any separated tissue therein; and (E) means linking said actuator and said stylet for longitudinal movement as a unit extending through both said longitudinal cavities, said actuator upon actuation causing via said linking means sliding movement of said stylet between said proximal position and said distal position.

11. The assembly of claim 10 wherein said cutting member distal end defines a distal recess as means for separating biopsy tissue from the patient as said cutting member is moved distally and maintaining the separated tissue in said distal recess.

12. The assembly of claim 10 wherein said longitudinal cavity in said cutting member communicates with said side recesses and said flexible member longitudinal cavity, said assembly additionally including means operatively secured to the other of said opposed flexible member ends for applying a vacuum to said recesses via said cutting member longitudinal cavity.

* * * * *